United States Patent [19]

Nelson et al.

[11] Patent Number: 4,663,961
[45] Date of Patent: May 12, 1987

[54] SYSTEM FOR REMOTE CHEMICAL ANALYSIS

[75] Inventors: Robert L. Nelson, Orrville, Ohio; Frederick M. Ryan, Loyalhanna Township, Westmoreland County, Pa.

[73] Assignee: Westinghouse Electric Corp., Pittsburgh, Pa.

[21] Appl. No.: 777,108

[22] Filed: Sep. 17, 1985

[51] Int. Cl.⁴ ............................................. G01N 29/02
[52] U.S. Cl. ........................................................ 73/24
[58] Field of Search ............. 73/590, 643, 24, 61.1 R; 250/343, 353

[56] References Cited

U.S. PATENT DOCUMENTS 4,490,845 12/1984 Steinbruegge et al. ............. 250/339

OTHER PUBLICATIONS

G. Schmidtke et al., VDI-Berichte 509,293 (1984).

Primary Examiner—Stephen A. Kreitman
Attorney, Agent, or Firm—Thomas R. Trempus

[57] ABSTRACT

The improved system for remote chemical analysis of this invention includes a quartz halogen bulb as a source of infrared light, quartz fibers leading to and from a sample cell, a non-collinear thallium arsenic selenide, AOTF to perform spectral analysis and a lead selenide detector, Both the AOTF and the detector are interfaced with a microcomputer. Under the control of the microcomputer, this equipment gathers and interprets transmission spectra obtained through the passage of infrared light through the sample cell. Microcomputer interface provides rapid random-access to the RF frequency driving the AOTF, which selects the wavelength of light to be examined and also provides routines for sample averaging and the comparison of various reference spectra. An acousto-optic device mounted in an enclosure which includes input and output crystal fiber connectors is also provided.

10 Claims, 11 Drawing Figures

SYSTEM FOR REMOTE CHEMICAL ANALYSIS

BACKGROUND OF THE INVENTION

1. Field of the Invention

The invention is directed to both a system and a technique for remote chemical analysis. More particularly, the invention provides for the use of a solid-state acousto-optic device in combination with fiber optic technology in order to provide a system for the remote chemical analysis of a species of interest.

2. Description of the Prior Art

It is the conventional practice in the petrochemical industry, to utilize "in-line" sensors to affect chemical analysis. However, in such configurations, the presence of electrical or chemical sensors poses a significant threat to the safety of the area, from either explosions or from chemical contamination. As a result, such "in-line" sensors must be contained in approved explosion-proof enclosures. These enclosures represent an obvious significant cost to the petrochemical industry.

It has been suggested by G. Schmidtke, et al. VDI-Berichte 509,293 (1984) that a fiber optic system can be utilized to provide remote chemical analysis. This prior art system utilizes a diffraction grating and an array of detectors in a location remote from a sampling area.

Acousto-optic tunable filters (AOTF) have previously been used in spectral analysis as an effective device to measure dilute gas mixtures. An example of an automated AOTF infrared analyzer system which is unsable in a variety of industrial and commercial control applications is disclosed in U.S. Pat. No. 4,490,845 to Steinbruegge et al., which patent is assigned to the assignee of the present invention and incorporated herein by reference as if fully set forth.

Concentrated mixtures of gases and especially liquids often have strong, nearly total absorption bands. To analyze these mixtures, one must utilize the weaker overtone absorptions. These overtone bands lie in the near-to-intermediate infrared, where quartz fiber optic attenuation is not prohibitive to the use of such fibers. Using optical fibers eliminates one of the constraints with present detection systems.

It is an object of the present invention to provide a remote system for chemical analysis which utilizes optical fibers to convey an infrared source to a sample and then from the sample toward a detector array. This configuration would allow the use of such a remote chemical analysis system in applications where the presence of electrical or chemical sensors pose a significant threat from, for example, either explosions or from chemical contamination.

It is yet another object of this invention to provide an improved remote chemical analyzer which incorporates an automated acousto-optic infrared analyzer system remotely disposed from the sample site.

SUMMARY OF THE INVENTION

The invention provides an improved system for remote chemical analysis wherein a sample cell is disposed in a location remote from the means whereby the analysis is effected. The system of this invention includes a sample cell adapted to receive therein a species of interest to be analyzed which species has predetermined infrared absorption characteristics. The sample cell has window means on opposed sides thereof for the passage of light therethrough. An infrared light source is coupled to a first optical fiber which, in turn, is coupled to one window of the sample cell. Means for focusing the light from the infrared light source to the first optical fiber are also included as are means for directing the light conveyed through the first optical fiber through the sample cell. Typically, these means comprise lenses. A second optical fiber is disposed between the sample cell and an acoustooptic tunable filter analyzer system. There are means for focusing the infrared radiation after modification by the absorption characteristics in the sample cell onto the second optical fiber which transmits the so-modified infrared radiation to the acousto-optic device. An infrared detector to measure the intensity of the diffracted light and a microprocessor to interface the support electronics to the acousto-optic device and the detector are also provided. This microprocessor also provides the capability of storing and examining the data obtained.

In an alternative embodiment to this configuration, an acousto-optic tunable filter (AOTF) would be positioned on the source side proximate the source of infrared radiation so that the only light sent through the fiber would be the pulsed light of the desired frequency. This configuration could tend to improve the signal-to-noise ratio. An apparatus is provided which houses an acousto-optic device and includes connector means for RF input to the acousto optic device and integral input and output fiber optic connectors.

BRIEF DESCRIPTION OF THE DRAWINGS

The above, as well as the other features and advantages of the present invention, can be more readily appreciated through consideration of the detailed description of the invention in conjunction with the several drawings in which.

DETAILED DESCRIPTION OF THE INVENTION

Figure 1:
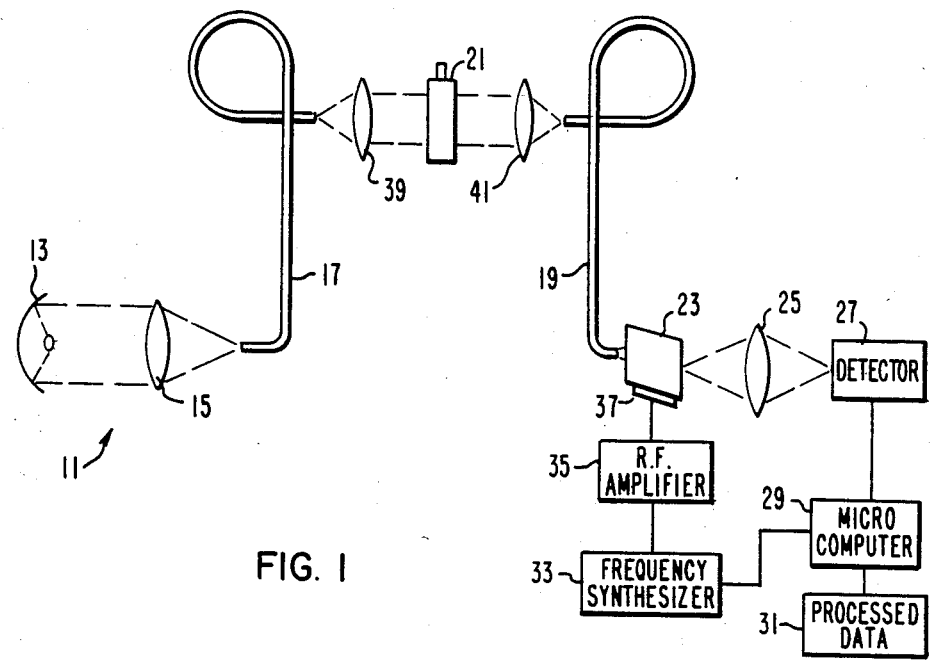
FIG. 1 is a schematical representation of a first embodiment of the remote chemical analysis system all according to the teachings of this invention.
Figure 2:
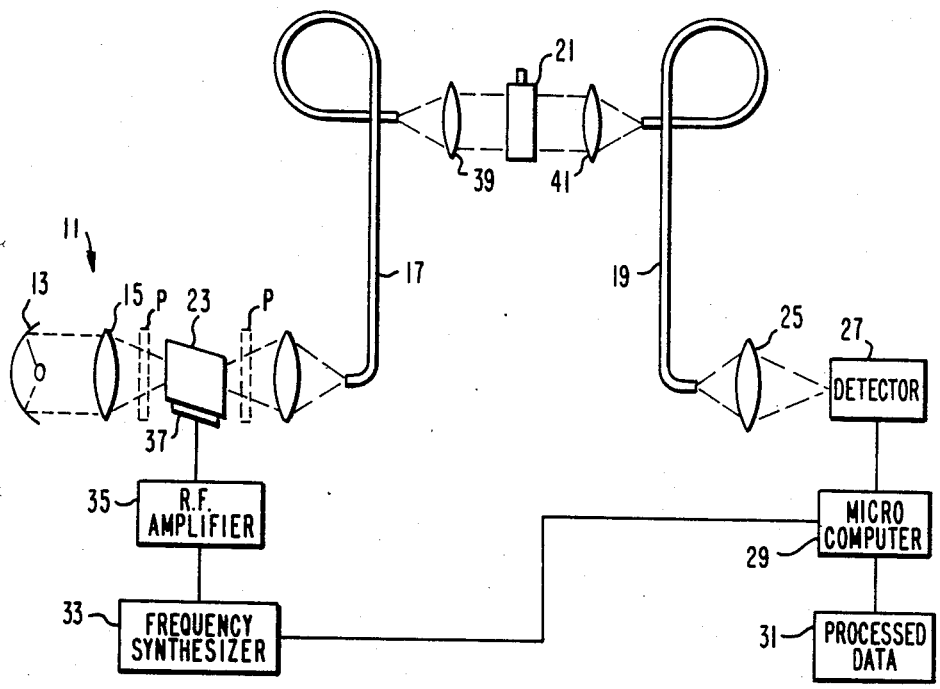
FIG. 2 is a second embodiment of the remote chemical analysis system of this invention in which an acousto-optic tunable filter is disposed on the source side of the sample cell.
Figure 3:
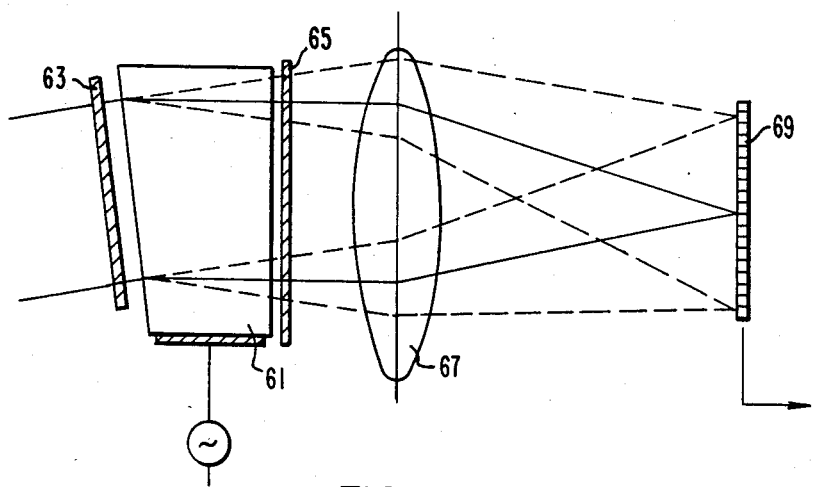
FIG. 3 is a schematical view of the detection scheme of a further alternative embodiment of this invention incorporating the acousto-optic dispersive light filter AODLF.

The invention provides an improved system for remote chemical analysis. A block diagram of several embodiments of this system are shown in FIGS. 1, 2 and 3. The system shown in FIG. 1 was prepared as a model in order to test the feasibility of this concept. The block diagrammatic system shown in FIG. 2 represents a preferred embodiment utilizing an AOTF for commercial application. FIG. 3 illustrates a further alternative embodiment with an AODLF and detector array. It should be appreciated that each embodiment provides an extremely useful improved system for remote chemical analysis. The description of the acousto-optic tunable filter which is incorporated into the system will be presented in detail hereinafter in conjunction with the description of FIG. 4. Accordingly, reference is made to that section with additional information concerning the structure and operation of the acousto-optic tunable filter (AOTF).

Turning now to FIG. 1, there is shown a block diagram of the expanded system for remote chemical analysis generally indicated by the reference character 11. This system can be visualized in three sections for ease of discussion. The first section contains an infrared source 13 and optics 15 to couple the light into a first optical fiber 17. The second section consists of the first fiber optic section 17 and a second fiber optics section 19 as well as a remotely positioned sample cell generally indicated at 21. While a sample cell was utilized in the testing of this system it is to be appreciated that the fiber optic sections 17 and 19 can be incorporated into a conduit means through which a process stream is conveyed. Accordingly, the term sample cell means is to be understood to include both of the aforedescribed concepts. This sample cell means would be connected through the optical fibers to the infrared source and the infrared detection means. The third section contains the infrared detection means. The third section contains the infrared analyzer which includes the acousto-optic tunable filter 23 coupled directly to the optical fiber 19 which conveys the infrared radiation which has been modified by the absorption characteristic of the sample species. Optics as at 25 are disposed between the AOTF 23 and an infrared detector means 27 for focusing the output of the AOTF onto the detector. Support electronics are coupled to the detector and to the AOTF. These electronics include a microcomputer 29, a process data storage means 31, frequency synthesizer 33 and an RF amplifier 35 coupled to the transducer 37 which is, in turn, bonded to the acousto-optic crystal. A more detailed description of the electronics package that can be used in combination with an AOTF and infrared detector can be had in U.S. Pat. No. 4,490,845 entitled automated acousto-optic infrared analyzer system, which Patent is assigned to the assignee of the present application and which is incorporated herein by reference as if fully set forth.

As can be seen in FIG. 2, an alternative to the basic configuration described above can be had by incorporating the acousto-optic tunable filter at the source side of the sample cell. In this configuration, the AOTF 23' is disposed between a focusing means 15 for the infrared radiation source 13 and the optical fiber 17. Thus, the only light transmitted through optical fiber 17 is the pulsed light of the desired frequency as will be described hereinafter. This configuration would tend to help improve the signal-to-noise ratio and would be the desired placement for an AOTF based production model. In all other respects, like reference characters represent like components in the configurations of FIGS. 1 and 2. By way of explanation, the embodiment illustrated in FIG. 1 illustrates an actual layout which has been utilized to test the principles of this invention and is better suited to an experimental configuration, for the optics can be more easily aligned. FIG. 2 also includes optional polarizers 'P' disposed on either side of the AOTF in dashed line.

In a working model of this invention, the infrared light source 13 was a 2.8 volt, 0.8 amp quartz halogen flashlight bulb mounted in a parabolic reflector. This source proved easy to work with, stable, and produced a well collimated beam. The spectral emission of the bulb adequately covers the range necessary to implement this invention. The light from the beam was focused down into the end of an optical fiber by means of a 2-inch diameter calcium fluoride lens 15. The optical fibers and sample cell constitute the second section described above. The fibers used in the demonstration model were two 18-inch sections of a commercially available 1 mm quartz fiber. The length of the fiber used was sufficient to demonstrate the capabilities of this concept but short enough so that fiber attenuation had little or no effect on the total system response. A sample cell was connected between these two fibers 17 and 19. Calcium fluoride lenses were used to collimate the light input from one fiber and to refocus it onto the other. These lenses were generally indicated by the reference characters 39 and 41, respectively. Within this region of collimated light was a cell 21 to hold the species of interest. The cell consisted of two 4 mm thick sapphire windows separated by a 2 mm neoprene O-ring with an opening in the top thereof to allow a syringe to introduce and remove liquid into and from the cell 21. The area of the cell exposed to the light was approximately 10 $cm^2$ to give a total volume examined of approximately 2 cc. In further tests of this concept, the lens assembly comprising lenses 39 and 41 has been replaced by two plano-convex quartz lenses attached directly to the sapphire windows of the cell 21. This arrangement minimizes alignment difficulties. The light having been modified by the absorptive characteristics of the species contained within the cell is brought back from the cell 21 to the analysis system consisting of the AOTF, detector means, etc. by means of the quartz fiber 19. The working model of this remote chemical analyzer utilized an Apple II microcomputer to interface the TAS AOTF with the support electronics and to enable, through an analog-to-digital converter, the collection and storage of data from the infrared detector means 27. The support electronics referred to herein and described in detail by the referenced U.S. Patent, are used to supply pulsed RF drive to the AOTF 23 and consist of a low power frequency synthesizer capable of generating RF output up to 150 MHz, an electronic gate to pulse the signal to the amp, and a high power RF amplifier.

During testing, the AOTF was driven by a 10 $\mu s$ pulse at a duty cycle of 1%. The final peak-to-peak voltage across the transducer was approximately 30 volts. The maximum strength of the diffracted light arrived at the detector 5 $\mu s$ after the pulse ended, at which time the computer recorded the data from the detector. The frequency synthesizer scanned the range from 80 MHz to 130 MHz in 200 KHz steps. At each step, 255 samples were taken from the detector and averaged to minimize system noise. The data for the entire scan was then stored in a disk file and could be plotted to give the spectral response of the system and the sample.

The system illustrated in FIGS. 1 and 2 utilizes a non-collinear thallium arsenic selenide ($Tl_3AsSe_3$ or TAS), AOTF to perform spectral analysis and a lead selenide detector, both interfaced with the aforedescribed microcomputer. The acousto-optic tunable filter can also utilize a TeO₂ crystal. Under microcomputer control this equipment gathered and interpreted the transmission spectra. The microcomputer interface provided rapid random access to the RF frequency driving the AOTF, which selected the wavelength of light examined, and also provided routines for sample averaging and the comparison of various reference spectra. The number of liquids and gases both organic and inorganic, with overtone absorptions in the near and intermediate infrared allows this device to cover a wide range of applications. The tunable nature of the AOTF allows the implementation of relatively simple or potentially complex algorithms for analyzing spectra. Also possible is the ability to switch quickly to an alternate range of absorptions at higher concentrations for more accuracy.

Figure 4:
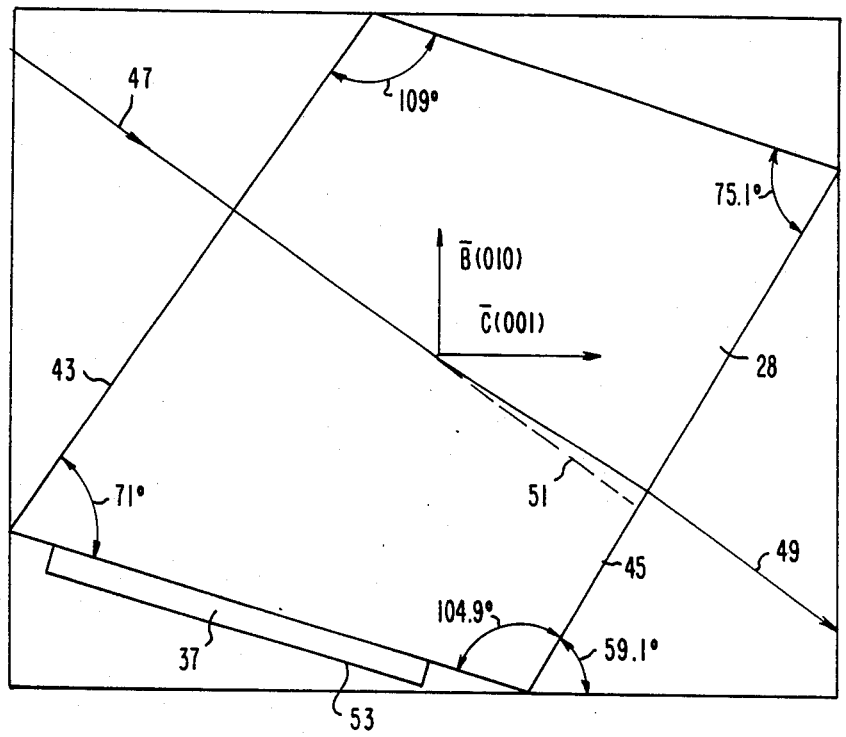
FIG. 4 is a comprehensive illustration of the design of an acousto-optic tunable filter used in an embodiment of this invention.

A small TAS crystal was cut and polished for use as an AOTF in this system. A rather schematic illustration of this TAS crystal is shown in FIG. 4. The TAS crystal was selected for use because of its good transmission in the infrared from 1.3 $\mu$s to 17.0 $\mu$s and its relatively high acousto-optic "figure to merit". The filter is designed to work in the non-collinear mode of operation, in which the incident light propagates at an angle to the acousto-wave front in the crystal. Although non-collinear AOTF's generally have a lower resolution than collinear filters, the spectra of concentrated gases and liquids are sufficiently broad that the reduced resolution in the non-collinear mode is still acceptable. The non-collinear AOTF also provides a spatial separation between the beam diffracted by the acoustic waves and the light transmitted straight through, thus simplifying the gathering of the light transmission data. The small crystal employed has a large angular aperture for the input light, and could capture the light supplied by a fiber directly attached to the crystal without the need for intermediate optics.

As can be seen in FIG. 4, the cross-section of the crystal 25 is a distorted parallelogram. The slant of the crystal properly orients the input face 43 and the output face 45 of the crystal to the path of the light 47, and allows for acoustic beam walkoff. The input face 43 was designed to be normal to the incident light from the fiber, i.e., 47, and the output face 45 was designed so that the diffracted light emerges parallel to the incident light, but displaced on the order of 1 mm. The deflected signal is indicated at 49 while that light which is not affected throgh acoustic interaction is indicated by the dashed line 51.

A 30° rotated x-cut lithium niobate crystal plate was indium bonded to the crystal under pressure to the surface of the crystal to serve as the transducer 37. A gold electrode was deposited on top of this at 53 and gold wire bonds connected the transducer by an appropriate connector. The resolution of the filter is determined, among other parameters, by the interaction length between the light and the acoustic path. In the crystal illustrated, that is approximately equal to the length of the transducer which is 5 mm.

The alternative embodiment illustrated in FIG. 3 incorporates the acousto-optic dispersive light filter and detector array in lieu of the previously described acousto-optic tunable filter and detector for the AOTF and detector shown in FIG. 1. The acousto-optic dispersive light filter 61 is an electronically adjustable spectroscopic device capable of instantaneously monitoring many wavelengths with a fixed drive frequency. The AODLF is functionally very similar to a fixed grating, but there are several important differences which are advantageous. The two principle differences are the tunability of the AODLF and its birefrigent operation. The AODLF is unique in that it allows for the electronic tunability of the grating constant, which allows flexibility of operations, such as large changes of spectral range. The electronic tunability also easily permits the frequency modulation of the optical signal in order to perform derivative spectroscopy, which may improve the signal-to-noise ratio over that of a constant signal. The schematic representation of the spectrum analyzer utilizing the AODLF as shown in FIG. 3 (in combination with FIG. 1) includes input and output polarizers 63 and 65 respectively, a focusing lens 67 and a photodetector array 69 for measuring the spectral information. A thallium arsenic selenide acousto-optic dispersive light filter is described in pending U.S. patent application Ser. No. 666,416 filed Oct. 30, 1984 and assigned to the assignee of the present invention.

Turning now to FIG. 5, the key element for the use in the improved system for remote chemical analysis of this invention is shown in several embodiments. The combined acousto-optic device with fiber optic connectors is shown in the structure indicated by the reference character 71. The structure 71 includes a housing 73 which supports the acousto-optic device 23 therein. As can be seen the transducer 37 is coupled to the RF drive means by means of an RF connector 75 on the external housing 73. Fiber optic couplers 77 and 79 are disposed on opposite sides of the housing 73 so as to be in direct communication with the input and output faces respectively of the acousto-optic device 23. The fiber optic connectors 77 and 79 are commercially available. As can be seen in the schematic representations of FIGS. 5A, 5B, 5C and 5D, several internal configurations of this device are possible.

Figure 5A:
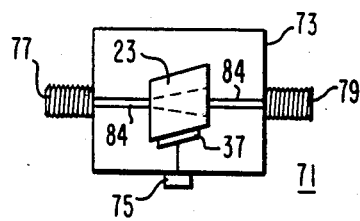
FIGS. 5A, B, C and D are illustrations of the design of the acousto-optic device with filter optic inputs used in this invention.
Figure 5B:
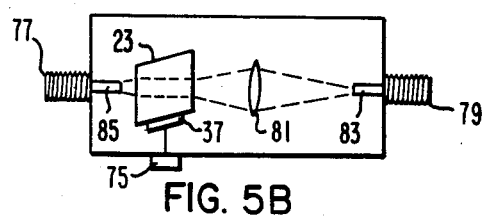
Figure 5C:
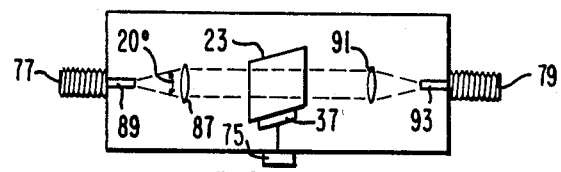
Figure 5D:
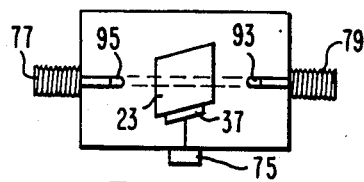

In FIG. 5A, both the input and output fiber-optic members 84 are butted up to the crystal input and output faces respectively. Infrared transmissive cement can also be employed to mate the optical fibers with the crystal. In FIG. 5B, the fiber-optic member 85 is spaced from the acousto-optic device 23. It can typically be expected that the output light from the fiber-optic member has a spread of roughly 20°. This spread however has no adverse affect on the resolution of the acousto-optic device. A lens 81 is disposed adjacent the output face of the crystal 23 to match the acceptance angle of the fiber-optic member 83 with the acousto-optic device 23 output. The diffracted light is thus focused onto the focal plane defined at the fiber-optic member 83. The undiffracted light output of the acousto-optic device 23 is spatially separated on that focal plane. In the configuration shown in FIG. 5C, the first lens indicated at 87 would serve to collimate the light output from the fiber 89 while a second lens 91 near the output face of the crystal 23 would serve to focus the diffracted light onto the cable 93. Finally, in FIG. 5D graded index lenses 95 and 93 which are dimensioned for use with fiber optics and commercially available under the trademark SELFOC from Nippon Glass can be employed in lieu of the more conventional lenses described above in connection with FIGS. 5B and 5C. Accordingly, it should be appreciated that in the embodiments shown in FIGS. 1-3, the acousto-optic device 23 and associated lenses are representative of the apparatus 71 shown in FIG. 5. Thus the various combinations of both graded index lenses as well as more conventional lenses and fiber optics can be used in this apparatus to achieve the desired result.

Experimental Use

Figure 6:
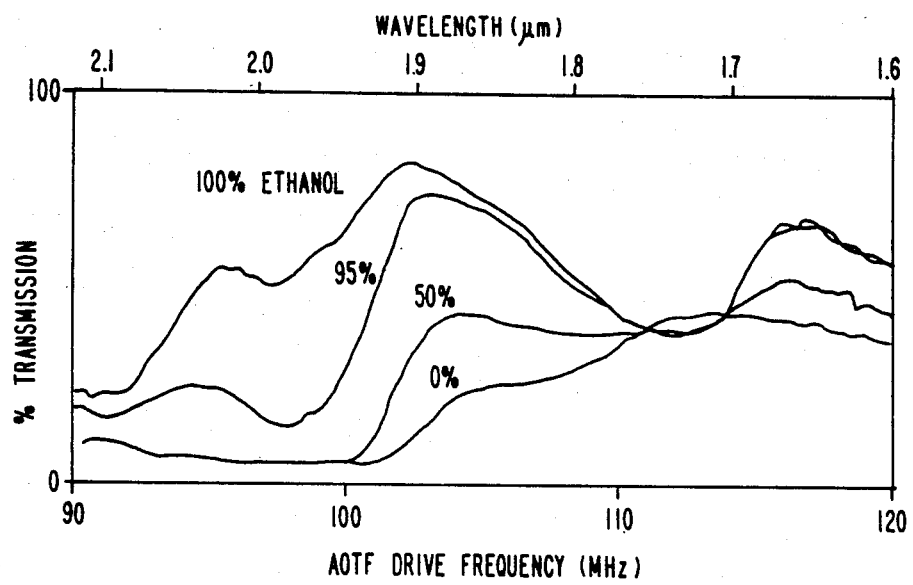
FIG. 6 is a graph presenting the percent of transmission for various concentrations of ethanol in water.
Figure 7:
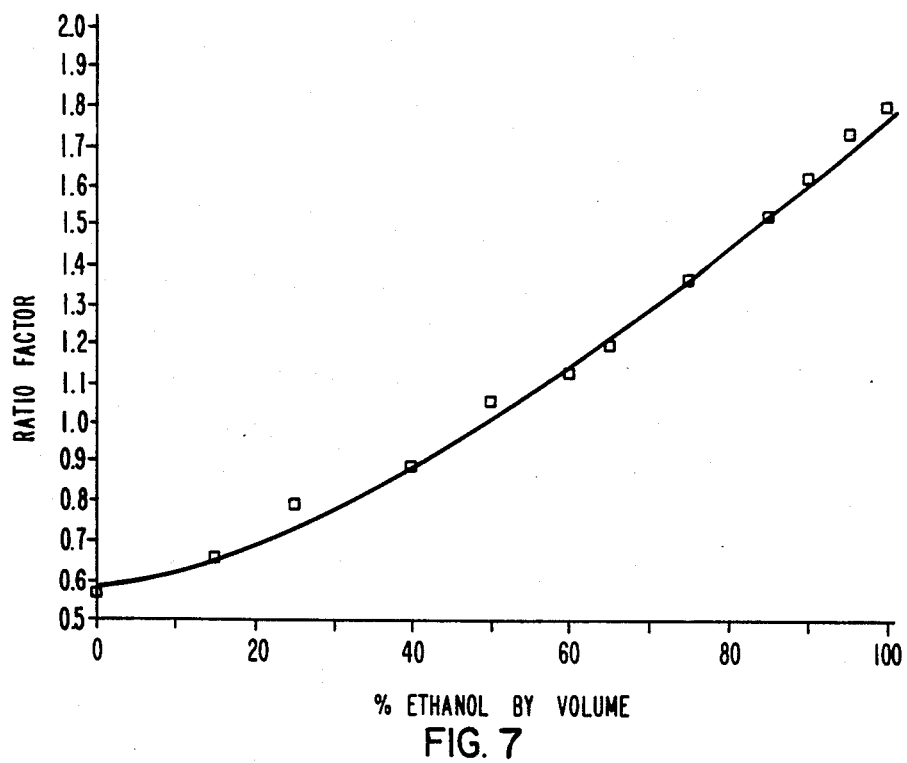
FIG. 7 is a graph presenting a calibration curve base on data obtained through a system of this invention.
Figure 8:
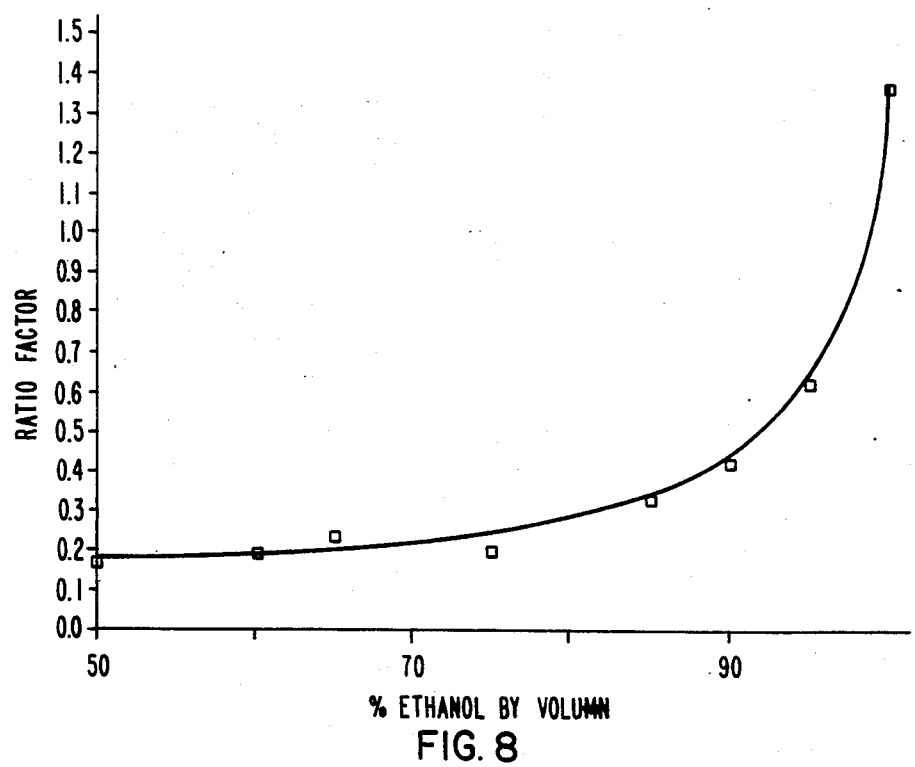
FIG. 8 is a graph presenting the calibration curve for concentrations of ethanol above 75%.

The system as discussed in conjunction with FIGS. 1 and 4 was tested by determining the concentration of ethanol in an ethanol-water mixture. A reference spectrum against which all further spectra were normalized and ratioed was first established by testing the system with no sample in the sample cell. After a system response was obtained, samples of various concentrations of ethanol in water mixtures were analyzed. Their spectra were ratioed and stored. A sample algorithm was developed to indicate the percentage of ethanol in the mixtures and at the same time cancel out some of the effects upon the data from the system. Such effects would include a dropoff at longer wavelengths which can be attributed to the reduced output of the halogen bulb and, in a small part, to the attenuation of quartz fibers. It should be obvious that additional algorithms can be utilized to compensate for these factors. In each case, during the testing, the spectral transmission for an ethanol and water mixture was obtained and then ratioed against the reference spectrum. This resulted in the percent transmission of light throughout the wavelength range measured with respect to an empty cell. The percent transmission for a pure ethanol, a 50% ethanol and a pure water mixture are shown in FIG. 6. It can be seen from these spectra that the transmission at 105 MHz rose evenly with an increase in the percent ethanol, while the transmission at 113 MHz dropped slightly. The algorithm involved taking the ratio of the percent transmission at these frequencies to each other, and using this ratio to determine the percent of ethanol. Data was gathered over a wide range of concentrations and the resulting calibration curve is shown in FIG. 7. It was also seen in the spectra that in concentrations of ethanol greater than 75%, it was more accurate to observe the ratio between 95 MHz and 113 MHz. The transmission rose sharply at 95 MHz as the water became more dilute, due to a very strong absorption by water at the corresponding wavelength of light. The calibration curve for concentrations of ethanol above 75% is shown in FIG. 8. The system could conceivably be programmed to switch to this more accurate ratio when it detected concentrations above a minimum limit by the first method.

As a test of the algorithm, several samples from a household liquor cabinet were obtained for analysis. The mixtures selected were relatively clear and covered the range from 12 to 47% ethanol content by volume. The spectra from these samples were obtained and analyzed as above, and the resolution ratios were used to estimate the percent alcohol in the mixture, based on a least square exponential curve fit of the calibration data. The results of the unknown and the estimated percentages are given in Table I.

TABLE I

DETERMINATION OF UNKNOWNS
Calibration formula:
% Ethanol - 85.8 · ln 1.76 · (Ratio 105/113 MHz)

| Unknown | Determined Ratio of % transmission at 105 MHz/113 MHz | Predicted Percentage Ethanol | Percentage Ethanol by label |
|---|---|---|---|
| Gordon's Gin | 1.016 | 49.4 | 47 |
| Bacardi Rum | .932 | 42.5 | 40 |
| Heublein Gin | .890 | 38.6 | 34 |
| M&R Vermouth | .730 | 21.6 | 18 |
| Keknyelu White Wine | .693 | 17.1 | 12 |

The calculated percentages of these samples were slightly higher than the listed percentages given on the labels, which could result in several factors. First, the examples examined were not pure ethanol and water mixtures, although samples as close to this as possible were used. The most significant offset in the data was at the lower percentages. These samples were white wines, which have a greater amount of contaminants and are less strictly measured for alcohol content than higher ethanol content beverages. Unfortunately, no samples above 50% ethanol were readily availale, although we expect results from such mixtures to have a higher accuracy.

What has been described is an acousto-optic tunable filter spectral analyzer connected to a separate "in-line" sensor by fiber optics which is used to measure concentrations of liquid mixtures having overtone absorptions in the near-to-intermediate infrared. While modifications and improvements to this system are planned, the feasibility of such a system has been established. The composition of liquid or concentrated gas samples can be examined in a sample cell safely removed from the electrical system by fiber optics. The absence of electricity near the sensing cell negates the need for expensive enclosures for the sensor, making this device highly suited to industries such as petroleum processing. In addition, the solid-state construction of the AOTF system lowers the change of both misalignment and component wear.

What is claimed is:

1. An improved system for remote chemical analysis wherein a sample species is disposed in a location remote from the means whereby the analysis is effected comprising:

a sample cell means adapted to receive therein or convey therethrough a species of interest to be analyzed which species has predetermined infrared absorption characteristics, said sample cell means having window means on opposed sides thereof for the passage of light therethrough;

an infrared light source;

an acousto-optic tunable filter analyzer system, which system comprises an acousto-optic tunable filter having an optically aligned acousto-optic crystal through which the infrared radiation is passed at a predetermined angle relative to the crystal optic axis, an acoustic transducer means coupled to a variable frequency rf energy source and to the acousto-optic crystal to launch acoustic waves into the crystal to interact with a selected narrow bandwidth portion of the infrared radiation to make it distinguishable from the remaining infrared radiation, which selected narrow bandwidth portion is a function of the frequency of the rf energy and acoustic waves;

means for focusing light from said infrared light sorce onto said acousto-optic tunable filter at the predetermined angle;

at least a first optical fiber which transmits the selected narrow bandwidth portion from the acousto-optic crystal to said sample cell;

a second optical fiber disposed between said sample cell means and an infrared radiation detection means;

said infrared radiation detection means generating an output signal as a function of the output filter infrared radiation having passed through said sample cell means;

computing means to which the detection means output signal is applied for determining the species present in said sample cell means and including means for the pulsed operation of the rf energy source to determine timing and frequency of rf energy applied to the acoustic transducer made into the acousto-optic crystal to determine the infrared wavelength selectivity for tuning of the acousto-optic tunable filter.

2. The improved system for remote chemical analysis according to claim 1 wherein the acousto-optic tunable filter is a thallium arsenic selenide crystal.

3. The improved system for remote chemical analysis according to claim 1 wherein the acousto-optic tunable filter includes polarizers disposed on the input and output sides of the crystal.

4. An improved system for remote chemical analysis wherein a sample species is disposed in a location remote from the means whereby the analysis is effected comprising:

a sample cell means adapted to receive therein or convey therethrough a species of interest to be analyzed which species has predetermined infrared absorption characteristics, said sample cell means having window means on opposed sides thereof for the passage of light therethrough;

an infrared light source;

a first optical fiber;

means for focusing light from said infrared light source into said first optical fiber which is in communication with said sample cell means;

a second optical fiber disposed between said sample cell means and an acousto-optic dispersive light filter (AODLF) analyzer system;

means for focusing the infrared radiation after modification by the absorption characteristic of the sample species onto said second optical fiber for the transmission of the so-modified infrared radiation to said AODLF analyzer system; and said AODLF analyzer system including an optically birefrigent crystal having an optical input face, and optical output face said optical input face being disposed a predetermined angle which is normal to the incident light, means acoustically coupled with one of said sides for launching acoustic waves into said crystal at a predetermined fixed frequency wherein each wavelength resolution element which emerges from the optical output face is at a different diffracted angle, and wherein the predetermined angle of the optical input face is selected such that for the fixed acoustic frequency, there is a minimum in the Bragg angle with frequency, while the diffracted Bragg angle increases linearly with frequency, an acoustic transducer means coupled to a variable frequency rf energy source and to the crystal to launch acoustic waves into the crystal;

an infrared radiation detector array which detects the output infrared radiation from the acousto-optic dispersive light filter and generates an output signal as a function of the output filtered infrared radiation; and computing means to which the detection means output signal is applied for determining the species present in the sample cell and including means for the pulse operation of the rf energy source to determine timing and frequency of rf energy applied to the acoustic transducer mated to the acousto-optic crystal to determine the infrared wavelength selectivity for tuning of the acousto-optic tunable filter.

5. The improved system for remote chemical analysis according to claim 4 wherein the acousto-optic tunable filter is a thallium arsenic selenide crystal.

6. The improved system for remote chemical analysis according to claim 4 wherein the acousto-optic tunable filter includes polarizers disposed on the input and output sides of the crystal.

7. An acousto-optic device for spectral analysis use in a fiber optic system comprising:

a housing defining an enclosure in which is mounted an acousto-optic device having an optically aligned acousto-optic crystal through which radiation is passed at a predetermined angle relative to the crystal optic axis, an acoustic transducer means coupled to the acousto-optic crystal to launch acoustic waves into the crystal to interact with a selected narrow bandwidth portion of the radiation to make it distinguishable from the remaining radiation, which selected narrow bandwidth portion is a function of the frequency of an RF energy drive in communication with said transducer means;

optical fiber input connector means disposed on a side of said housing proximate the input face of the acousto-optic crystal and adapted to removably receive thereon an optic fiber;

optical fiber connector output means disposed in said housing approximate the output face of said crystal and adapted for interconnection with an optical fiber; and RF connector means disposed on said housing and in electrical communication with said acoustic transducer means of said acousto-optic crystal and adapted to be coupled to an RF energy source.

8. The acousto-optic device according to claim 7 including lens means disposed in said housing between the input connector and the input face of the acousto-optic crystal.

9. The acousto-optic device according to claim 8 including lens means disposed in said housing between the output face of the crystal and the output optical connector means.

10. The acousto-optic device according to claim 7 including lens means disposed in said housing between the output face of the crystal and the output optical connector means.

* * * * *